United States Patent
Baker

[11] Patent Number: 6,165,973
[45] Date of Patent: Dec. 26, 2000

[54] FLUORESCENT WHITENING AGENT, ITS PREPARATION AND USE

[75] Inventor: Richard Leon Baker, Mobile, Ala.

[73] Assignee: Ciba Specialty Chemicals Corporation, Tarrytown, N.Y.

[21] Appl. No.: 09/493,341

[22] Filed: Jan. 28, 2000

Related U.S. Application Data

[60] Provisional application No. 60/118,821, Feb. 5, 1999.

[51] Int. Cl.[7] .............................. C09K 11/06; C11D 3/00; C11D 15/00; D06L 3/00
[52] U.S. Cl. ........................ 510/516; 510/518; 510/461; 252/301.21; 252/301.23
[58] Field of Search .................................... 510/516, 518, 510/461; 252/301.21, 301.23

[56] References Cited

U.S. PATENT DOCUMENTS

3,766,083  10/1973  Langstroth et al. ............. 252/301.2 W (List continued on next page.)

FOREIGN PATENT DOCUMENTS

841189  7/1960  United Kingdom .

(List continued on next page.)

*Primary Examiner*—Yogendra Gupta
*Assistant Examiner*—John M Petruncio
*Attorney, Agent, or Firm*—Kevin T. Mansfield

[57] ABSTRACT

A fluorescent whitening agent comprising a mixture of compounds of the formulae Ia, Ib and Ic:

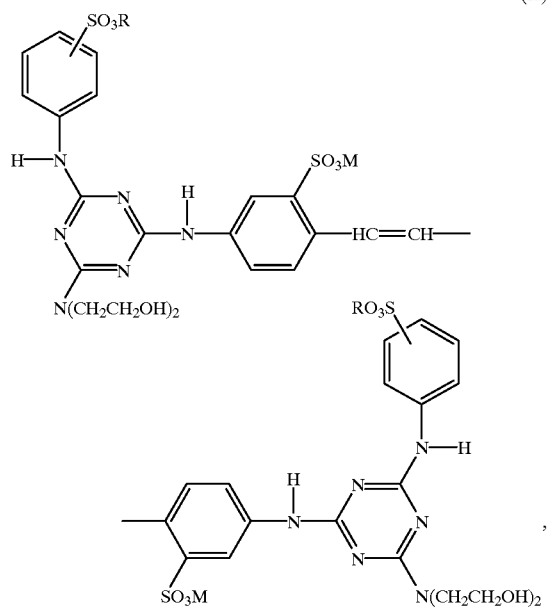

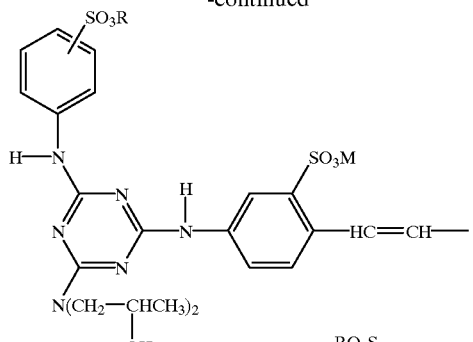

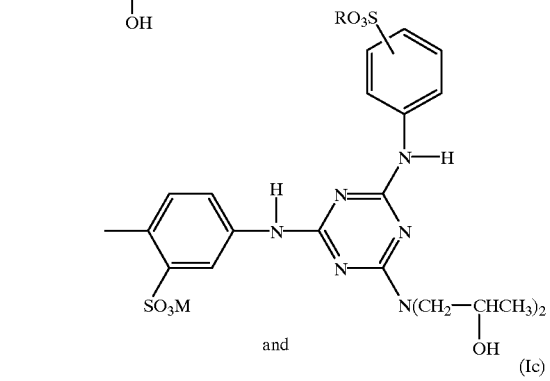

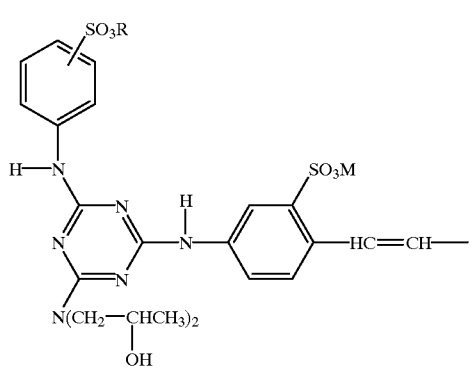

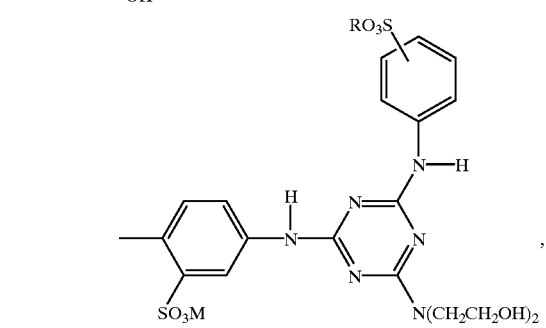

in which the —$SO_3R$ groups are in the meta and/or para position, and wherein R and M, independently of each other are H, Na, Li, K, Ca, Mg, ammonium, or ammonium that is mono-, di-, tri- or tetra-substituted by $C_1$–$C_4$alkyl, $C_1$–$C_4$-hydroxyalkyl or a mixture thereof, a process for its preparation and its use to brighten paper and especially textile materials.

23 Claims, No Drawings

U.S. PATENT DOCUMENTS

| | | | |
|---|---|---|---|
| 3,853,583 | 12/1974 | Langstroth et al. | 117/33.5 T |
| 4,339,238 | 7/1982 | Fringeli et al. | 8/527 |
| 4,388,079 | 6/1983 | Suzuki et al. | 8/648 |
| 4,468,341 | 8/1984 | Beyer | 252/301.23 |
| 5,051,111 | 9/1991 | Anceschi et al. | 8/648 |
| 5,688,758 | 11/1997 | Reinehr et al. | 510/516 |
| 5,800,862 | 9/1998 | Kaufman et al. | 427/458 |

FOREIGN PATENT DOCUMENTS

| | | |
|---|---|---|
| 896533 | 5/1962 | United Kingdom . |
| 1211812 | 11/1970 | United Kingdom . |
| 1512076 | 5/1978 | United Kingdom . |

FLUORESCENT WHITENING AGENT, ITS PREPARATION AND USE

This application claims benefit of provisional application No. 60/118,821, filed Feb. 5, 1999.

The present invention relates to a fluorescent whitening agent, a process for its preparation and its use to brighten textile materials. More particularly it relates to a fluorescent whitening agent which is a mixture comprising 3 different diaminostilbene disulfonic acid-type fluorescent whiteners, a process for the preparation of this fluorescent whitening agent and its use to brighten paper and especially textile materials.

Fluorescent whitening agents have been used for decades to create intense, bright white shades in textiles, plastics and paper.

One important class of fluorescent whitening agents is based on triazine derivatives of 4,4'-diaminostilbene-2,2'-disulfonic acid. Many such compounds are known and a number of them are commercially available. However there is still a need for improved fluorescent whitening agents for various applications.

GB-A 841,189 and 896,533 teach certain symmetrical triazine derivatives of 4,4'-diaminostilbene-2,2'-disulfonic acid wherein the triazinyl moieties are substituted by diethanolamino or diisopropanolamino groups, respectively.

GB-A 1 512 076 discloses an optical brightening agent for cellulosic and polyamide fabrics and paper which is a mixture of 2 or 3 triazine derivatives of 4,4'-diaminostilbene-2,2'-disulfonic acid. The mixture comprises one or two symmetrically substituted compounds and a third one having 2 different triazine radicals which correspond to each of the radicals in the 2 symmetrical ones. This 3 component optical brightening agent is prepared by condensing a mixture of 2-methoxy-4,6-dichloro-sym-triazine and 4,6-dichloro-2-(m- or p-sulfophenylamino)-sym-triazine or its sodium salt with 4,4'-diaminostilbene-2,2'-disulfonic acid or its disodium salt, to obtain a 3 component intermediate mixture, and then reacting this mixture with an aliphatic, aromatic or heterocyclic amine or ammonia to obtain the final optical brightening agent.

Now, however, a new fluorescent whitening agent which comprises a mixture of 3 triazine derivatives of 4,4'-diaminostilbene-2,2'-disulfonic acid—two symmetrically substituted ones and a third one having 2 different triazine radicals which correspond to each of the radicals in the 2 symmetrical ones, has been discovered. The new fluorescent whitening agent uses different reactants than those taught in the GB-A 1 512 076 patent and is prepared via a different synthetic sequence. This new fluorescent whitening agent shows distinct advantages in whitening paper and textile materials over the separate components and over other state of the art triazinyl diaminostilbene disulfonic acid-type fluorescent whitening agents.

Thus in one aspect the present invention relates to a fluorescent whitening agent which comprises a mixture of compounds of the formulae Ia, Ib and Ic:

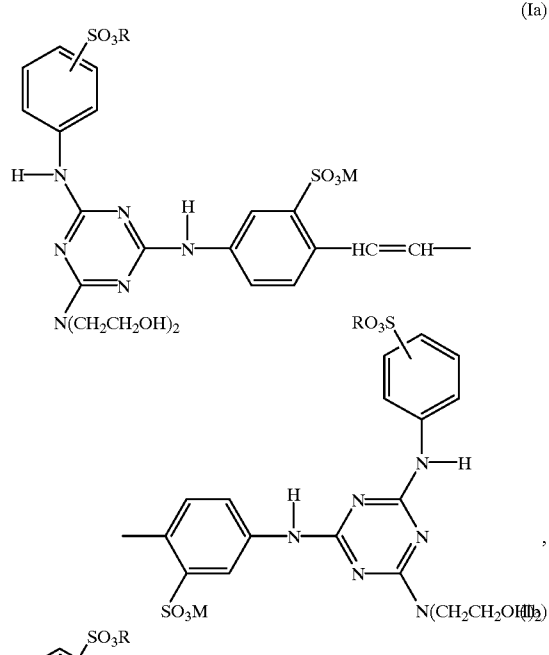

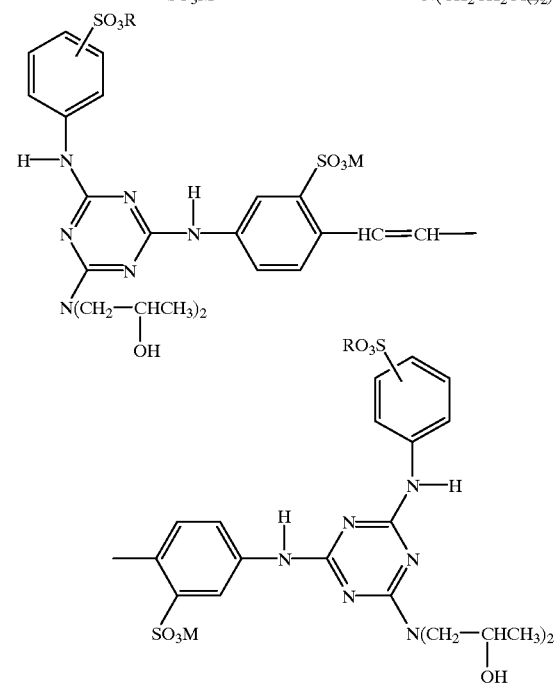

and

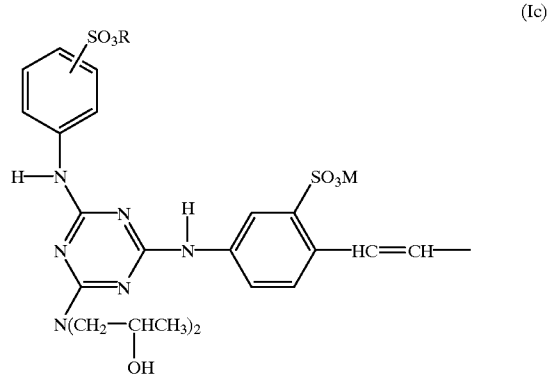

-continued

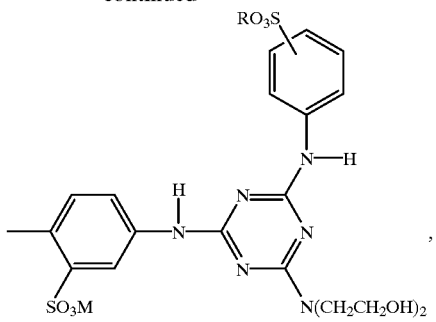

in which the —SO₃R groups are in the meta and/or para position, and wherein R and M, independently of each other are H, Na, Li, K, Ca, Mg, ammonium, or ammonium that is mono-, di-, tri- or tetra-substituted by $C_1$–$C_4$alkyl, $C_1$–$C_4$-hydroxyalkyl or a mixture thereof.

The —SO₃R groups are preferably in the meta position.

When R and/or M is ammonium that is monosubstituted by $C_1$–$C_4$alkyl, it is preferably methyl-, ethyl-, n-propyl-, isopropyl-, n-butyl- or tert.-butylammonium. When R and/or M is ammonium that is disubstituted by $C_1$–$C_4$alkyl, it is preferably dimethyl-, diethyl-, di-n-propyl-, diisopropyl-, or di-n-butylammonium. When R and/or M is ammonium that is trisubstituted by $C_1$–$C_4$alkyl, it is preferably trimethyl- or triethylammonium. When R and/or M is ammonium that is tetrasubstituted by $C_1$–$C_4$alkyl, it is preferably tetramethyl-, tetraethyl-, methyltributyl- or tetrabutylammonium.

When R and/or M is ammonium that is mono-, di-, tri- or tetra-substituted by $C_1$–$C_4$hydroxyalkyl, it is preferably diethanol-, disopropanol- or triethanolammonium, with triehanolammonium being particularly preferred.

When R and M are the same, they are preferably Na.

Preferably R and M are different. In particular it is preferred that M is Na, Li or K, with Na being particularly preferred. Preferably R is ammonium that is di- or trisubstituted by $C_1$–$C_4$hydroxyalkyl, with triethanolammonium being particularly preferred. Naturally, since R and M are the counterions of sulfo groups, equilibration of the cations is to be expected. Nevertheless, compounds of the formulae Ia, Ib and Ic having, on average, about two triethanolammonium cations and two of sodium are especially preferred.

Compounds of the formulae Ia, Ib and Ic can be prepared by reacting the appropriate starting materials in any order. They are advantageously prepared by a process which comprises:

a) reacting 2 moles of cyanuric chloride with 4,4'-diaminostilbene-2,2'-disulfonic acid in the presence of an acid acceptor;

b) reacting the bis(4,6-dichloro-sym-triazinyl) product from step a) with a total of about 2 moles of diethanolamine and diisopropanolamine to give a mixture of compounds of the formulae IIa, IIb and IIc;

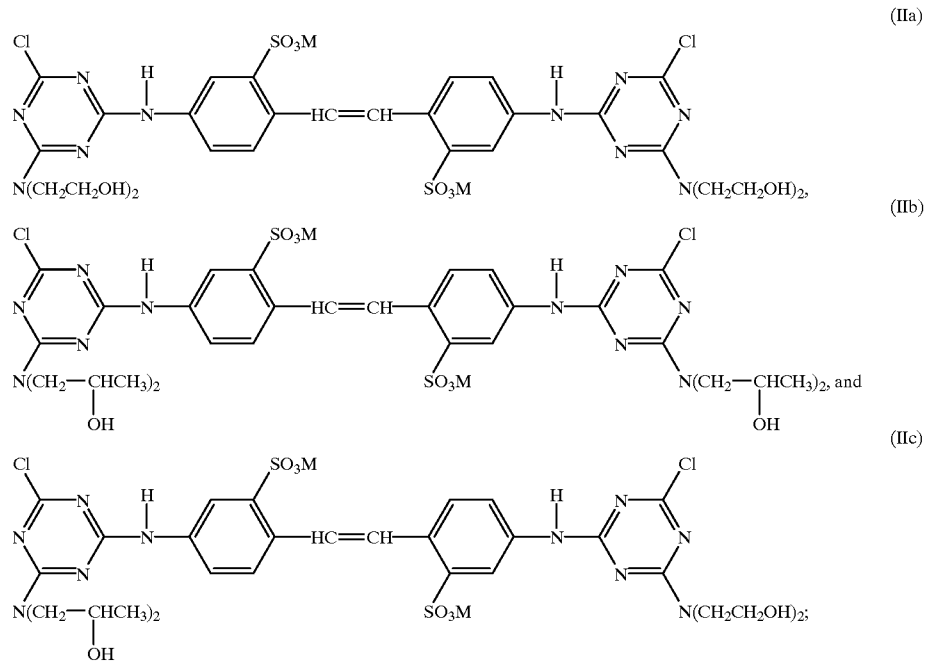

c) reacting the product mixture from step b) with about 2 moles of sulfanilic and/or metanilic acid and, optionally d) neutralizing the product formed with a base such as NaOH, LiOH, KOH, CaO or Ca(OH)₂, MgO or Mg(OH)₂, ammonia, a primary, secondary or tertiary $C_1$–$C_4$alkyl- or alkanolamine or a tetra-$C_1$–$C_4$alkylammonium hydroxide.

The inventive fluorescent whitening agent can be obtained in solid form or as a stable liquid concentrate. Preferably, if it is to be isolated as a solid, the product formed in step c) is neutralized with an inorganic base such as NaOH. If it is to be isolated as a stable liquid concentrate, preferably it is neutralized with an organic base, in particular an alkanolamine.

The first reaction step is preferably carried out by adding 4,4'-diaminostilbene-2,2'-disulfonic acid to a slurry of cyanuric chloride in an aqueous organic medium, preferably a water/methyl ethyl ketone mixture, at −5 to 10° C., preferably 0 to 5° C., in the presence of a sufficient amount of acid acceptor to maintain a pH of about 4–6. Any alkali metal or alkaline earth metal hydroxide, bicarbonate or carbonate is suitable as an acid acceptor, but an aqueous sodium carbonate solution (about 20% w/w) is preferred.

The second reaction step to give the mixture of compounds of the formulae IIa, IIb and IIc is carried out by adding, per mole of the bis(4,6-dichloro-sym-triazinyl) product from step a), from 0.5 to 1.5 moles of diethanolamine and from 0.5 to 1.5 moles of diisopropanolamine, with the total amount of the amines being at least about 1.9 moles. The total amount of the amines is advantageously from 2.0 to 2.3 moles. Preferably a small excess of the amines is employed to drive the reaction to completion. Preferably from 0.75 to 1.25 moles of diethanolamine and from 0.75 to 1.25 moles of diisopropanolamine is employed; most preferably about equimolar amounts of the amines are employed.

The diethanolamine and diisopropanolamine may be added simultaneously in separate streams or premixed. They may also be added sequentially in any order. Preferably they are added simultaneously as a mixture. Following the amine addition, the temperature is raised to 35 to 65° C., preferably 45 to 55° C., while maintaining the pH between about 7.5 and 8.

Preferably, the crude mixture of compounds of the formulae IIa, IIb and IIc is separated from the organic solvent, e.g. methyl ethyl ketone, collected by filtration and then slurried in water. This product mixture is then reacted with 2 moles of sulfanilic or metanilic acid or a mixture thereof in the presence of an acid acceptor. Advantageously a small excess of sulfanilic and/or metanilic acid, for example a 10 to 30% excess, is employed to drive the reaction to completion. If R in the formulae Ia, Ib and Ic is an ammonium radical, for example a triethanolammonium radical, then the corresponding amine, for example triethanolamine, is advantageously employed as the acid acceptor.

When a mixture of sulfanilic and metanilic acid is employed, each of the formulae Ia, Ib and Ic represents a mixture of 3 compounds in which the —$SO_3R$ groups are in the meta, para and meta/para positions. When a mixture of sulfanilic and metanilic acid is employed it comprises 5–95% of sulfanilic acid, preferably 30–70% and 95–5% of metanilic acid, preferably 70–30%.

The starting materials are known and in most cases are commercially available.

Depending on the proportions of the amines added in step b) and whether they are added simultaneously or sequentially, the proportions of the compounds of the formulae IIa, IIb and IIc formed in this step, and hence the amounts of the compounds of the formulae Ia, Ib and Ic will vary considerably. When from 1.9 to 2.3 moles of equimolar amounts of diethanolamine and diisopropanolamine are added simultaneously, the compounds of the formulae IIa, IIb and IIc are formed in the approximate molar ratios of 25% of the compound of the formula IIa, 25% of the compound of the formula IIb and 50% of the compound of the formula IIc.

When from 1.9 to 2.3 moles of a mixture of diethanolamine and diisopropanolamine are added simultaneously, but employing a 50% molar excess of diethanolamine, the compounds of the formulae IIa, IIb and IIc are formed in the approximate molar ratios of 35–40% of the compound of the formula IIa, 10–15% of the compound of the formula IIb and 45–50% of the compound of the formula IIc. When from 1.9 to 2.3 moles of a mixture of diethanolamine and diisopropanolamine are added simultaneously, but employing a 50% molar excess of diisopropanolamine, the compounds of the formulae IIa, IIb and IIc are formed in the approximate molar ratios of 15–20% of the compound of the formula IIa, 30–35% of the compound of the formula IIb and 45–50% of the compound of the formula IIc.

When from 1.9 to 2.3 moles of equimolar amounts of diethanolamine and diisopropanolamine are added sequentially, the amount of the compounds of the formulae IIa and IIb are enriched at the expense of the compound of the formula IIc. For example, when the diethanolamine is added first and allowed to react, followed by the diisopropanolamine, the compounds of the formulae IIa, IIb and IIc are formed in the approximate molar ratios of 40% of the compound of the formula IIa, 40% of the compound of the formula IIb and 20% of the compound of the formula IIc. If further enrichment of the compounds of the formulae IIa and/or IIb is desired, additional amounts of the compounds of the formulae IIa and/or IIb, which can be readily prepared by adding about 2 moles of only one of the amines in step b), can be added.

As is evident from the discussion above, depending on the amounts and proportions of the amines added in step b) and whether they are added simultaneously or sequentially, the proportions of the compounds of the formulae IIa, IIb and IIc formed in step b), and hence the amounts of the compounds of the formulae Ia, Ib and Ic in the fluorescent whitening agent can be varied considerably. Thus the present invention relates to a fluorescent whitening agent which comprises a mixture of the compounds of the formulae Ia, Ib and Ic wherein they are present in the approximate molar ratios of 10–45% of the compound of the formula Ia, 10–45% of the compound of the formula Ib and 15–50% of the compound of the formula Ic, and to a process in which they are formed in said molar ratios. Preferably the fluorescent whitening agent comprises the compounds of the formulae Ia, Ib and Ic in the molar ratios of 15–35% of the compound of the formula Ia, 15–35% of the compound of the formula Ib and 35–50% of the compound of the formula Ic. Most preferably the fluorescent whitening agent comprises the compounds of the formulae Ia, Ib and Ic in the molar ratios of 20–30% of the compound of the formula Ia, 20–30% of the compound of the formula Ib and 45–50% of the compound of the formula Ic.

The fluorescent whitening agent of the present invention is applied to paper and especially to textile materials, in particular to cellulose-containing textile materials such as cotton and cotton-containing blends, by methods and in amounts which are conventional for similar compounds. Thus the fluorescent whitening agent can be applied to cotton at the 0.1 to 2% by weight level by exhaustion from an aqueous liquor or from a peroxide-containing bleaching bath. It is particularly preferred to employ the fluorescent whitening agent of the present invention at the 0.1 to 2% by weight level in a continuous bleaching process. The fluorescent whitening agent detergent of the present invention may also be advantageously incorporated into solid and liquid laundry detergent compositions.

The fluorescent whitening agent of the present invention shows distinct advantages in whitening paper and especially textile materials over the separate components and over other state of the art triazinyl diaminostilbene disulfonic acid-type fluorescent whitening agents. Compared to other alternatives, it exhibits good buildup in whiteness with increasing concentrations of the fluorescent whitening agent, good pH stability, good stability to washing out from textile materials even at high temperatures and a particularly desirable blue-white shade.

In the following Examples, parts are parts by weight unless indicated otherwise. Said Examples are merely illustrative and the invention is not limited thereto.

EXAMPLE 1

Step 1; reaction of cyanuric chloride with 4,4'-diaminostilbene-2,2'-disulfonic acid Into a two liter flask equipped with an agitator, pH probe, thermometer and condenser is charged 400 mls. of methyl ethyl ketone and 200 g. ice. The mixture is cooled to about −5° C. To the vigorously stirred mixture is then added 50 g. of cyanuric chloride. The pH is then increased from about 2.5 to about 4–6 by gradual addition of an aqueous 20% w/w sodium carbonate solution. While maintaining a temperature of 0 to 5° C. with external cooling, 401 mls. of a 12% w/v solution of 4,4'-diaminostilbene-2,2'-disulfonic acid is added to the slurry of cyanuric chloride over a period of 16 minutes. About 16 mls. of additional 12% w/v solution of 4,4'-diaminostilbene-2,2'-disulfonic acid is added over about 10 minutes while testing for the disappearance of cyanuric chloride by TLC. The addition is halted when cyanuric chloride is no longer detected.

Step 2, reaction of bis(4,6-dichloro-sym-triazinyl) product from step 1 with mixture of diethanolamine and diisopropanolamine Into a two liter flask equipped with an agitator, pH probe, thermometer and condenser is charged 1523 g. of a step 1 reaction mixture containing 147.9 g. of the step 1 bis(4,6-dichloro-sym-triazinyl) product and having a pH of 6. Upon addition of a mixture of 21.49 g. of diethanolamine and 32.04 g of an 85% by weight solution of diisopropanolamine to the mixture with intensive mixing, the pH quickly rises above 9, then begins to drop. The pH is maintained at 7.5–8.0 by the simultaneous addition of 50% sodium hydroxide solution while heating the mixture to 50° C. The reaction mixture is then stirred at about 50° C. and pH 7.5–8.0 for 30 minutes. Then 76.8 g. of sodium chloride is added and the methyl ethyl ketone removed by simple distillation to a final pot temperature of 100° C. The slurry is then cooled to about 25° C. and collected by vacuum filtration to give 418.8 g of wet cake having 45.9% solids. The wet cake is used "as is", i.e. without drying in the next step.

Step 3, reaction of the product mixture from step 2) with metanilic acid and neutralization Into a two liter flask equipped with an agitator, pH probe, thermometer and condenser is charged 264.4 g. of a step 2 reaction mixture having 47.4% solids followed by 350 ml. of water. To the stirred mixture is added 47.14 g. of metanilic acid followed by 40.7 g. of triethanolamine, whereupon the pH rises from below 3 to about 6–7. The reaction mixture is then heated to about 90° C. and mixed for 2 hours. The viscous reaction mixture is then cooled to about 70° C. and 48.53 g. of triethanolamine is added. The resulting solution is then cooled to about 40° C. and clarified by filtration.

EXAMPLE 2

Step 3 is repeated as above, except that metanilic acid is replaced by the same amount of sulfanilic acid. There is obtained a solution of the compounds of the formulae Ia, Ib and Ic in which the —SO$_3$R groups are in the para position.

EXAMPLE 3

Step 3 is repeated as in Example 1, except that metanilic acid is replaced by the same amount of a 50:50 mixture of metanilic acid and sulfanilic acid. There is obtained a solution of the compounds of the formulae Ia, Ib and Ic which has the —SO$_3$R groups in the meta, para and meta/para positions.

EXAMPLE 4

Evaluation of the inventive fluorescent whitening agent on cotton

The following is a short description of the procedure used to evaluate the wash out properties of optical brighteners on cotton textile fabrics.

Square swatches of 100% cotton knit fabric weighing 10 grams are bleached at 100° C. for 90 minutes in a bleach bath formulation containing, per 1000 g. (1 liter):

15.36 g. 50% sodium hydroxide,
4.34 g. Ultravon® EL (nonionic surfactant),
5.11 g. Stabilon® NS New (bleach stabilizer),
14.57 g. sodium silicate,
70.40 g. 30% hydrogen peroxide and
0.2, 0.4, 0.8, 1.6, 2.4, 3.2 or 4.8 g of the fluorescent whitening agent of Example 1, at a liquor ratio 12:1. Ultravon EL and Stabilon NS New are available from Ciba Specialty Chemicals Corp., High Point, N.C.

The bleached samples are then removed, washed at a liquor ratio of 25:1 and neutralized as follows.

Cold wash: 3 washes for 5 minutes each at 27° C. and neutralization at pH 6.0–6.5, at 27° C. for 5 minutes.

Hot wash: 2 washes for 8 minutes each at 82° C.; 1 wash for 8 minutes at 71° C.; 1 wash for 8 minutes 49° C. and neutralization at pH 6.0–6.5, at 27° C. for 5 minutes.

The swatches are allowed to air dry and the Hunter Whiteness (see Hunter, Richard S., "Achieving accuracy in Measurement of Textiles for Reflectance and Whiteness", American Dyestuff Reporter 50, October 16, 1961) is measured for each sample.

Swatches subjected to bleaching in the presence of 1% on the weight of the fabric of the fluorescent whitening agent of Example 1 have a Hunter Whiteness of 148 after cold washing and 140.5 after hot washing.

What is claimed is:

1. A fluorescent whitening agent which comprises a mixture of compounds of the formulae Ia, Ib and Ic:

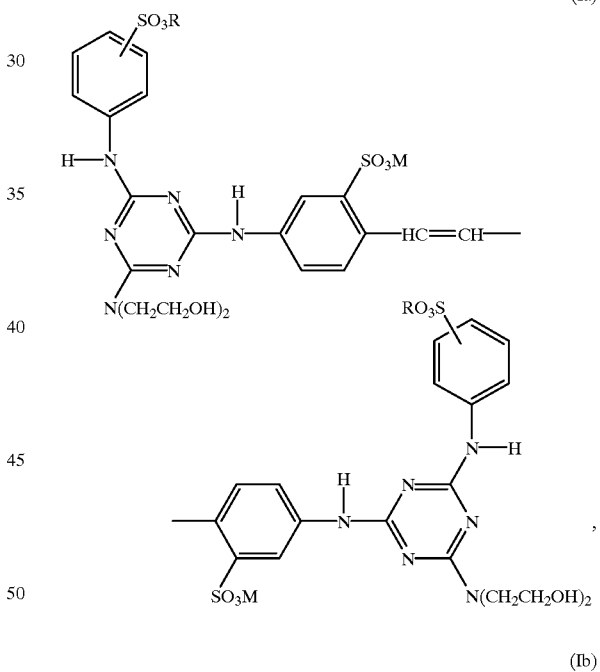

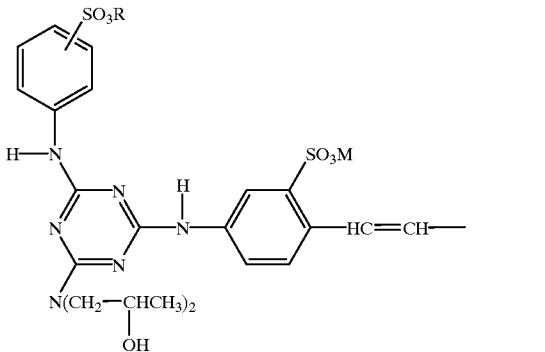

-continued

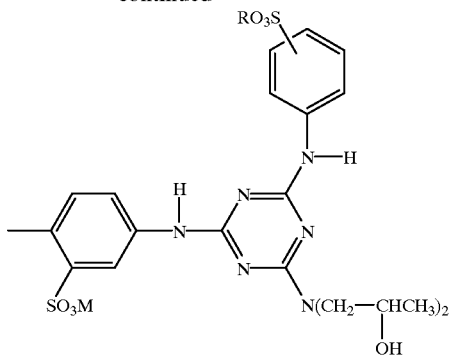

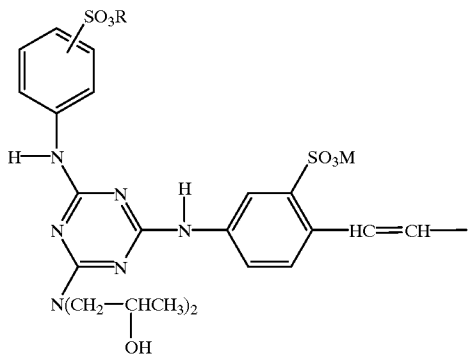

and

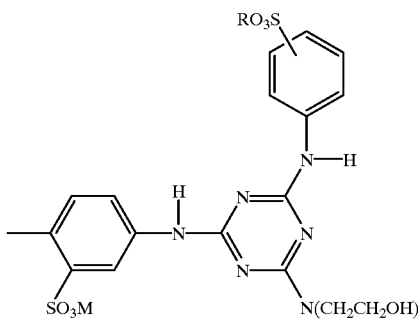

in which the —SO$_3$R groups are in the meta and/or para position, and wherein R and M, independently of each other are H, Na, Li, K, Ca, Mg, ammonium, or ammonium that is mono-, di-, tri- or tetra-substituted by C$_1$–C$_4$alkyl, C$_1$–C$_4$-hydroxyalkyl or a mixture thereof.

2. A fluorescent whitening agent according to claim 1, wherein the —SO$_3$R groups are in the meta position.

3. A fluorescent whitening agent according to claim 1, wherein R and/or M as ammonium that is monosubstituted by C$_1$–C$_4$alkyl is methyl-, ethyl-, n-propyl-, isopropyl-, n-butyl- or tert.-butylammonium; or as ammonium that is disubstituted by C$_1$–C$_4$alkyl is dimethyl-, diethyl-, di-n-propyl-, diisopropyl-, or di-n-butylammonium; as ammonium that is trisubstituted by C$_1$–C$_4$alkyl is trimethyl- or triethylammonium or as ammonium that is tetrasubstituted by C$_1$–C$_4$alkyl is tetramethyl-, tetraethyl-, methyltributyl- or tetrabutylammonium.

4. A fluorescent whitening agent according to claim 1, wherein R and/or M as ammonium that is mono-, di-, or trisubstituted by C$_1$–C$_4$hydroxyalkyl is diethanol-, disopropanol- or triethanolammonium.

5. A fluorescent whitening agent according to claim 1, wherein R and M are the same and are Na.

6. A fluorescent whitening agent according to claim 1, wherein M is Na, Li or K and R is ammonium that is di- or trisubstituted by C$_1$–C$_4$hydroxyalkyl.

7. A fluorescent whitening agent according to claim 6, wherein M is Na and R is triethanolammonium.

8. A fluorescent whitening agent according to claim 1, which comprises a mixture of the compounds of the formulae Ia, Ib and Ic wherein they are present in the molar ratios of 10–45% of the compound of the formula Ia, 10–45% of the compound of the formula Ib and 15–50% of the compound of the formula Ic.

9. A process for the preparation of a fluorescent whitening agent comprising a mixture of compounds of the formulae Ia, Ib and Ic:

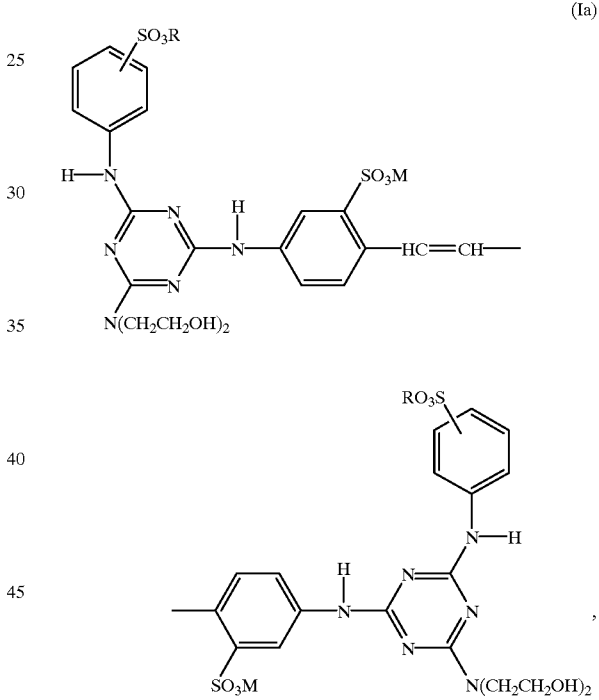

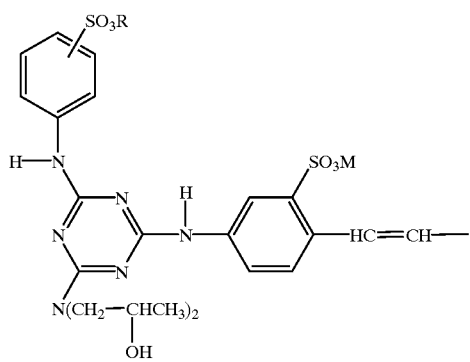

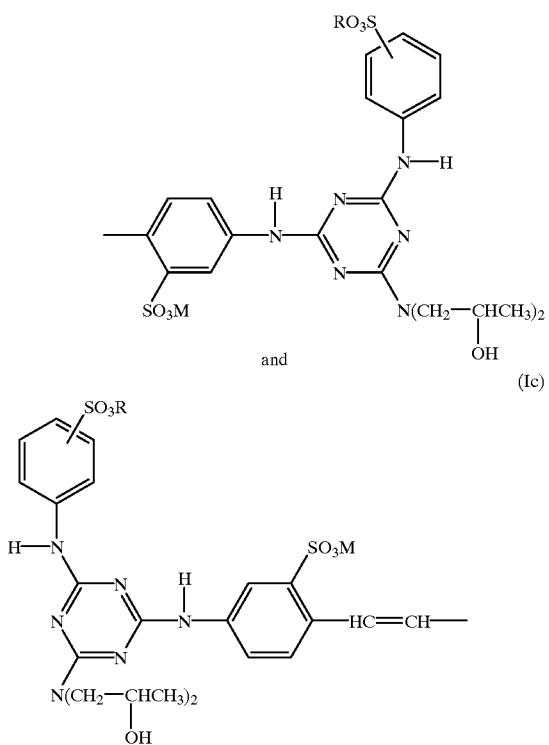

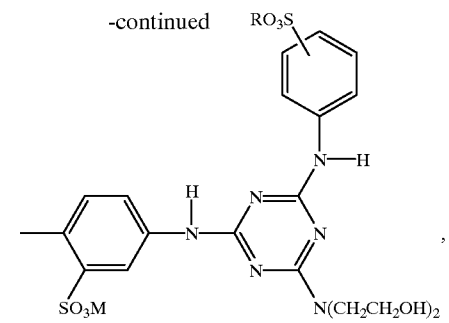

in which the —SO₃R groups are in the meta and/or para position, and wherein R and M, independently of each other are H, Na, Li, K, Ca, Mg, ammonium, or ammonium that is mono-, di-, tri- or tetra-substituted by $C_1$–$C_4$alkyl, $C_1$–$C_4$-hydroxyalkyl or a mixture thereof, which process comprises:

a) reacting 2 moles of cyanuric chloride with 4,4'-diaminostilbene-2,2'-disulfonic acid in the presence of an acid acceptor;

b) reacting the bis(4,6-dichloro-sym-triazinyl) product from step a) with a total of about 2 moles of diethanolamine and diisopropanolamine to give a mixture of compounds of the formulae IIa, IIb and IIc;

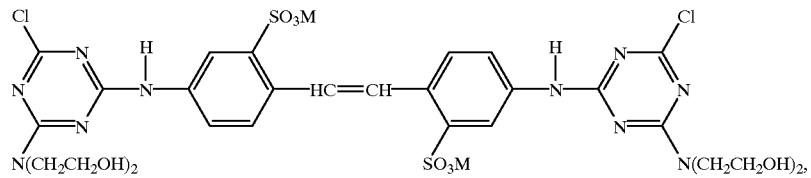

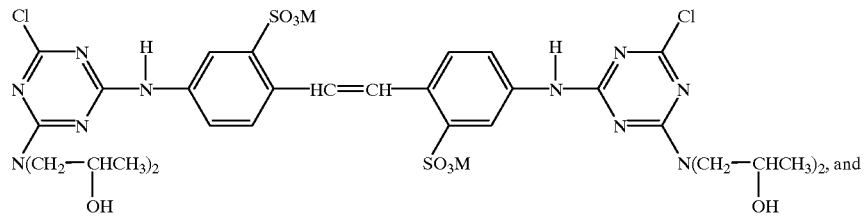

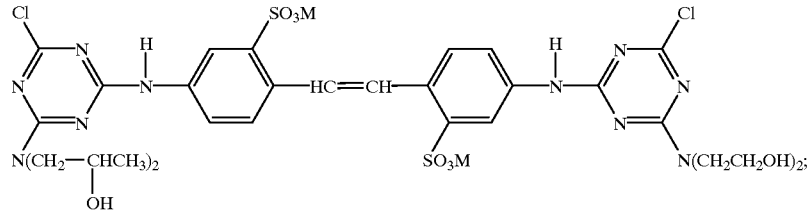

c) reacting the product mixture from step b) with about 2 moles of sulfanilic and/or metanilic acid and, optionally d) neutralizing the product formed with a base.

10. A process according to claim 9, wherein step b) is carried out by adding, per mole of the bis(4,6-dichloro-sym-triazinyl) product from step a), from 0.5 to 1.5 moles of diethanolamine and from 0.5 to 1.5 moles of diisopropanolamine, with the total amount of the amines being at least about 1.9 moles.

11. A process according to claim 10 wherein step b) is carried out by adding, per mole of the bis(4,6-dichloro-sym-triazinyl) product from step a), about equimolar amounts of diethanolamine and diisopropanolamine, with the total amount of the amines being at least about 1.9 moles.

12. A process according to claim 10, wherein the total amount of diethanolamine and diisopropanolamine added is from 2.0 to 2.3 moles.

13. A process according to claim 10, wherein step b) is carried out by adding the diethanolamine and diisopropanolamine simultaneously in separate streams or as a mixture.

14. A process according to claim 10, wherein step b) is carried out by adding the diethanolamine and diisopropanolamine sequentially in any order.

15. A process according to claim 9, wherein metanilic acid is employed in step c).

16. A process according to claim 9, wherein the product formed in step c) is neutralized with a base selected from the group consisting of NaOH, LiOH, KOH, CaO or $Ca(OH)_2$, MgO or $Mg(OH)_2$, ammonia, primary, secondary or tertiary $C_1$–$C_4$ alkyl- or alkanolamines and tetra-$C_1$–$C_4$ alkylammonium hydroxides.

17. A process according to claim 16, wherein the base is NaOH or triethanolamine.

18. A method of whitening paper or textile materials, which comprises applying to said materials an effective whitening amount of a fluorescent whitening agent according to claim 1.

19. A method according to claim 18, wherein the textile material is a cellulose-containing textile material.

20. A method according to claim 19, wherein the cellulose-containing textile material is cotton or a cotton-containing blend.

21. A method according to claim 19, wherein the fluorescent whitening agent is applied from a peroxide-containing bleaching bath.

22. A composition for bleaching and whitening cellulose-containing textile material which comprises an effective whitening amount of a fluorescent whitening agent according to claim 1.

23. A laundry detergent which comprises an effective whitening amount of a fluorescent whitening agent according to claim 1.

* * * * *

UNITED STATES PATENT AND TRADEMARK OFFICE
CERTIFICATE OF CORRECTION

PATENT NO.     : 6,165,973　　　　　　　　　　　Page 1 of 1
DATED          : December 26, 2000
INVENTOR(S)    : Richard Leon Baker It is certified that error appears in the above-identified patent and that said Letters Patent is hereby corrected as shown below:

On the title page, Section [75] should read:
--[75] Inventor: Richard Leon Baker, Mobile, Ala.--

Signed and Sealed this

Tenth Day of July, 2001

*Attest:*

NICHOLAS P. GODICI
*Attesting Officer*　　*Acting Director of the United States Patent and Trademark Office*